(12) United States Patent
Kang et al.

(10) Patent No.: US 7,964,018 B2
(45) Date of Patent: Jun. 21, 2011

(54) APPARATUS AND METHOD FOR COLLECTING AND DETECTING AIRBORNE PARTICLES

(75) Inventors: KyoungHo Kang, Hwaseong-si (KR); Yunwoo Nam, Yongin-si (KR); JungJoo Hwang, Suwon-si (KR); Alexsandr Danilovich Tolchinsky, Obolensk (RU); Vladimir Ivanovich Sigaev, Lenina (RU); Alexsander Nikolaevich Varfolomeev, Serpukhov (RU); Alexey Antonovich Mazhinsky, Lenina (RU); Pavel Konstantinovich Soloviev, Lenina (RU); Vadim Viktorovich Bunin, Lenina (RU)

(73) Assignee: Samsung Electronics Co., Ltd. (KR)

( * ) Notice: Subject to any disclaimer, the term of this patent is extended or adjusted under 35 U.S.C. 154(b) by 275 days.

(21) Appl. No.: 12/327,210

(22) Filed: Dec. 3, 2008

(65) Prior Publication Data
US 2009/0139399 A1 Jun. 4, 2009

(30) Foreign Application Priority Data

Dec. 3, 2007 (RU) ............................... 2007144523
Jun. 24, 2008 (RU) ............................... 2008125809

(51) Int. Cl.
*B01D 45/12* (2006.01)
(52) U.S. Cl. .................. 95/13; 95/187; 95/219; 96/245; 96/301; 96/306; 96/321; 96/413
(58) Field of Classification Search .............. 95/13, 187, 95/219; 96/243, 245, 301, 306, 321, 413
See application file for complete search history.

(56) References Cited

U.S. PATENT DOCUMENTS

| 4,092,845 | A | | 6/1978 | Prodi et al. |
| 4,144,759 | A | | 3/1979 | Slowik |
| 4,941,899 | A | | 7/1990 | Liu |
| 5,824,136 | A | * | 10/1998 | Meline .............................. 95/29 |
| 6,103,534 | A | | 8/2000 | Stenger et al. |
| 2004/0025963 | A1 | | 2/2004 | Squirrell et al. |

FOREIGN PATENT DOCUMENTS

| JP | 2007-069194 | 3/2007 |
| KR | 10-2004-0043560 | 5/2004 |
| KR | 10-2004-0050215 | 6/2004 |
| RU | 2 299 414 C1 | 5/2007 |
| RU | 2 299 415 C1 | 5/2007 |

OTHER PUBLICATIONS

Gennady I. Sigaev et al., "Development of a Cyclone-Based Aerosol Sampler with Recirculating Liquid Film: Theory and Experiment," Aerosol Science and Technology 40:5, Jun. 20, 2007, pp. 293-308, Taylor and Francis.

* cited by examiner

*Primary Examiner* — Robert A Hopkins
(74) *Attorney, Agent, or Firm* — Cantor Colburn LLP (57) ABSTRACT

An apparatus for collecting airborne particles includes a cyclone into which external air and an absorbing liquid are sprayed to absorb the airborne particles in the external air with the absorbing liquid, a reservoir in fluid communication with the cyclone and which stores the absorbing liquid to be sprayed into the cyclone as an absorbing liquid film, a collector in fluid communication with the cyclone and which collects the absorbing liquid film from the cyclone, and a feedback pipe in fluid communication with the collector and the reservoir and which transports the absorbing liquid film collected in the collector to the reservoir.

37 Claims, 7 Drawing Sheets

APPARATUS AND METHOD FOR COLLECTING AND DETECTING AIRBORNE PARTICLES

This application claims priority to Russian Patent Application Nos. 2007144523, filed on Dec. 3, 2007, and 2008125809, filed on Jun. 24, 2008, and all the benefits accruing therefrom under 35 U.S.C. §119, the contents of which in their entireties are herein incorporated by reference.

BACKGROUND

1. Field

The disclosure relates to an apparatus and method for collecting and detecting a concentration of airborne particles. More particularly, the disclosure relates to an apparatus which utilizes a cyclone to collect airborne particles mixed in external air by absorbing the airborne particles in an absorbing liquid and thereafter detecting a pollution level, e.g., a concentration of the airborne particles, in the absorbing liquid.

2. Description of the Related Art

Ambient air generally contains airborne substances such as airborne particles including microorganisms and/or dust, for example, which transmit diseases to human beings. In particular, crowded interior spaces such as office spaces and subways contain large amounts of airborne particles relative to less crowded or exterior spaces. Therefore, it is desired to measure a level of air contamination in interior spaces such as offices. To measure the level of air contamination, the airborne particles must be collected.

To collect the airborne particles, processes such as collision, gravitational and inertial precipitation, as well as filtering, electrification and condensation are typically used.

For example, collection of the airborne particles using collision is carried out by absorbing air containing airborne particles, e.g., micro materials, at a fast velocity to collide the micro materials against a culture plate. To provide the fast velocity, an inertial force and/or a friction force are utilized to facilitate collecting the micro materials. However, this method has inherent problems, in that it cannot be used repetitively, and a viability of any microbes in the micro materials is substantially reduced.

On the other hand, collection of micro materials using filtering is carried out by passing a predetermined volume of air through a filter to collect the micro materials on a surface of the filter. However, the filter method also has inherent problems in that frequent replacement of filters is required, and the method cannot be repeated easily, for example.

Collection of micro materials using electrification is typically accomplished by absorbing the micro materials on a surface of a filter using electrostatic attraction. However, this method is also problematic in that it requires additional components, such as an ion charger, for example.

Collection of micro materials using condensation is generally accomplished by absorbing micro materials mixed in air with atomized particles to condense the micro materials and thereby collect them in a liquefied state. In the condensation method, it is possible to collect viruses, and implement diverse detecting methods, but the condensation method also disadvantages, such as a requirement that to provide moisture and atomized particles for adsorption of the micro materials.

A lung simulating aerosol sampler, which is an apparatus for analyzing airborne particles aspirated from outside into a bubbler by a vacuum pump, has also been researched.

However, the abovementioned conventional samplers do not collect airborne particles in liquid medium, but merely measure the airborne particles using electrification, condensation or filtering, for example. Thus, conventional samplers are not well-suited for collecting airborne particles, and a collecting efficiency thereof is typically unacceptably low.

Thus, it is desired to develop an apparatus for efficient collection of airborne particles of microbiological origin.

SUMMARY

The disclosure was made to solve the above-mentioned problems occurring in the related art, and exemplary embodiments as described herein provide an apparatus for collecting airborne particles, particularly microbes, in liquid medium, wherein external air and absorbing liquid are efficiently supplied into a cyclone wherein an absorbing liquid is reused. Moreover, the absorbing liquid, to which the microbes are absorbed, and the external air are efficiently separated from each other to thereby provide a substantially increased collecting efficiency of microbes while effectively minimizing use of the absorbing liquid and at the same time maximizing viability of microbes collected. An operating principle of the apparatus according to an exemplary embodiment is based on inertial precipitation of airborne particles from a swirling air stream on a liquid film formed on an inner wall of a swirling chamber at the expense of an aspirated and atomized absorbing liquid. Liquid film rises up along an inner wall of a stripping column coaxially connected to the swirling chamber, and is thereafter accumulated in a tank.

An apparatus for collecting airborne particles according to an exemplary embodiment includes: a cyclone into which external air and an absorbing liquid are introduced for collecting the airborne particles in the external air with the absorbing liquid; a reservoir in fluid communication with the cyclone and which stores the absorbing liquid to be sprayed into the cyclone as an absorbing liquid film; a collector in fluid communication with the cyclone and which collects the absorbing liquid film from the cyclone; and a feedback pipe in fluid communication with the collector and the reservoir and which transports the absorbing liquid film collected in the collector to the reservoir.

The cyclone includes a swirling chamber and precipitating chamber, and the collector collects the absorbing liquid film flowing along an inner wall of the precipitating chamber. The swirling chamber has a cylinder shape.

The precipitating chamber has a shape of a truncated cone, and a lower portion of the precipitating chamber is coaxially connected to an upper portion of the swirling chamber.

The apparatus may further include an intake manifold in fluid communication with the cyclone. The intake manifold may include a first cylindrical channel and a second cylindrical channel disposed vertically adjacent to the first cylindrical channel, and a conical inlet nozzle common to both the first cylindrical channel and the second vertical channel. The intake manifold may be connected to the swirling chamber tangential to an inner diameter of the swirling chamber. Each of the first cylindrical channel and the second cylindrical channel includes a step change increase in a diameter thereof proximate to an outlet section thereof.

The first cylindrical channel is disposed above the second cylindrical channel, the first cylindrical channel includes an air ejector nozzle disposed proximate to the step increase in the diameter of the first cylindrical channel, and the second cylindrical channel includes a liquid ejector nozzle disposed proximate to the step increase in the diameter of the second cylindrical channel.

The reservoir may be detachably connected to the cyclone.

The collector may include a separator disposed apart from an upper portion of the precipitating chamber of the cyclone to separate flow of the absorbing liquid film from air flow in the cyclone, and a collecting tank which collects the absorbing liquid film separated by the separator.

The separator may have an annular shape which surrounds inner and outer walls of the precipitating chamber of the cyclone along a periphery of the upper portion of the precipitating chamber.

The collecting tank may include a spiral-shaped slant groove disposed in a lower surface thereof, and the feedback pipe may be connected to the collecting tank using the spiral-shaped slant groove.

The apparatus may further include a supply fitting connected to the reservoir, and the supply fitting may include a first inlet nipple, a second inlet nipple and a third inlet nipple.

The first inlet nipple of the supply fitting is connected to the collector by the feedback pipe.

The second inlet nipple of supply fitting is connected to a supply pipe to supply clean absorbing liquid to the reservoir.

The apparatus may further include a valve disposed in the supply pipe and which regulates an inflow of the clean absorbing liquid from an outer tank to the reservoir.

The apparatus may further include a drainage fitting connected to the reservoir, wherein the drainage fitting comprises a first outlet nipple, a second outlet nipple and a third outlet nipple.

A sensor for measuring a level of the absorbing liquid in the reservoir is connected to the first outlet nipple of the drainage fitting.

The apparatus may further include a detector in fluid communication with the reservoir and a sampling pipe connected to the second outlet nipple of the drainage fitting. The sampling pipe transports an aliquot of the absorbing liquid to the detector to detect a concentration of the airborne particles collected by the absorbing liquid film.

The apparatus may further include a valve disposed in the sampling pipe, wherein the valve regulates a flow of the absorbing liquid from the reservoir to the detector.

The apparatus may further include a drain pipe connected to the third outlet nipple of drainage fitting.

The apparatus may further include a valve disposed in the drain pipe, wherein the valve regulates a flow of the absorbing liquid from the reservoir to a waste tank.

The airborne particles may include microbes.

A method of collecting airborne particles according to an exemplary embodiment includes: supplying external air and an absorbing liquid to an internal space of a cyclone; mixing the external air and the absorbing liquid to form an absorbing liquid film on an inner wall of the cyclone; collecting airborne particles in the external air with the absorbing liquid film formed; collecting the absorbing liquid film in which the airborne particles are collected; and dispersing and remixing the absorbing liquid film with input airflow inside an intake manifold in fluid communication with the cyclone.

The supplying the external air and the dispersing and remixing the absorbing liquid film may be based on a pressure difference inside the cyclone.

The method may further include collecting an aliquot of the absorbing liquid to determine a concentration of the airborne particles collected by the absorbing liquid film.

The method may further include measuring one of a level and a degree of pollution of the absorbing liquid.

In an alternative exemplary embodiment, a system for collecting airborne particles and detecting a concentration of the airborne particles by absorbing the airborne particles into an absorbing liquid includes: a cyclone, into which external air from an air source and an absorbing liquid are introduced for collecting the airborne particles with the absorbing liquid, wherein the cyclone the external air and the absorbing liquid undergo vortex mixing and atomization to precipitate airborne particles from the external air onto a surface of liquid film formed inside the cyclone; a reservoir in fluid communication with the cyclone and which stores the absorbing liquid to be sprayed into the cyclone as an absorbing liquid film; a collector disposed at an upper part of the cyclone in fluid communication with the cyclone, which collects the absorbing liquid film moving along an inner wall of the cyclone and which transports the absorbing liquid film back to the reservoir; a supplementary reservoir connected to the reservoir and which supplies the absorbing liquid to the reservoir; a drain reservoir connected to the reservoir and which receives the absorbing liquid from the reservoir; and a detector connected to the reservoir and which measures a level of contamination of the absorbing liquid by sampling the absorbing liquid inside the reservoir.

The system may further include a level sensor connected to the reservoir and which detects a level of the absorbing liquid inside the reservoir. The level sensor may be a membrane pressure sensor.

The system may further include a three-way supply fitting disposed at an upper portion of the reservoir. Further, the three-way supply fitting may include a first inlet nipple connected to a feedback pipe connected between the collector and the reservoir, a second inlet nipple connected to a supply pipe connected to the supplementary reservoir, and a third inlet nipple connected to a first control pipe connected to the level sensor.

The system may further include a three-way drain fitting disposed at a lower portion of the reservoir, and the three-way drain fitting may include a first outlet nipple connected to a second control pipe connected to the level sensor, a second outlet nipple connected to a sampling pipe connected to the detector, and a third outlet nipple connected to a drain pipe connected to the drain reservoir.

The system may further include a microcontroller which controls an operation of a peristaltic filling pump, a peristaltic drain pump and a peristaltic sampling pump, based on electrical signals from at least one of the detector and the level sensor.

The microcontroller may include an analog-to-digital ("A/D") converter connected to the level sensor, a processor connected to the detector, switches connected to the peristaltic filling pump, the peristaltic drain pump and the peristaltic sampling pump, a relay connected to the air source, an input unit and a display.

A method for collecting airborne particles and detecting a concentration of the airborne particles according to an exemplary embodiment includes: supplying absorbing liquid to a reservoir; collecting the airborne particles in air with an absorbing liquid film supplied to a cyclone; sampling the absorbing liquid inside the reservoir to measure a level of contamination thereof; removing the absorbing liquid from the reservoir when the level of contamination thereof exceeds a predetermined value; and supplying new absorbing liquid to the reservoir.

The collecting airborne particles includes: mixing the absorbing liquid and air in an intake manifold; supplying the absorbing liquid and the air to a space inside the cyclone to form an absorbing liquid film therein; absorbing the airborne particles with the absorbing liquid film; collecting the absorbing liquid film containing the airborne particles in a collector; and resending the absorbing liquid film in the collector to the intake manifold to remix the absorbing liquid with the air.

The method further includes measuring a level of the absorbing liquid in the reservoir and supplying additional absorbing liquid to the reservoir when a level thereof decreases.

DETAILED DESCRIPTION

The disclosure will now be described more fully hereinafter with reference to the accompanying drawings, in which exemplary embodiments are shown. The embodiment may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the device in one of the figures were turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning which is consistent with their meaning in the context of the relevant art and the present disclosure, and will not be interpreted in an idealized or overly formal sense unless expressly so defined herein.

Exemplary embodiments are described herein with reference to cross section illustrations which are schematic illustrations of idealized embodiments. As such, variations from the shapes of the illustrations as a result, for example, of manufacturing techniques and/or tolerances, are to be expected. Thus, embodiments should not be construed as limited to the particular shapes of regions illustrated herein but are to include deviations in shapes which result, for example, from manufacturing. For example, a region illustrated or described as flat may, typically, have rough and/or nonlinear features. Moreover, sharp angles which are illustrated may be rounded. Thus, the regions illustrated in the figures are schematic in nature and their shapes are not intended to illustrate the precise shape of a region and are not intended to limit the scope of the present invention.

Hereinafter, a collecting apparatus for airborne particles according to an exemplary embodiment will be described in further detail with reference to the accompanying drawings.

Figure 1:
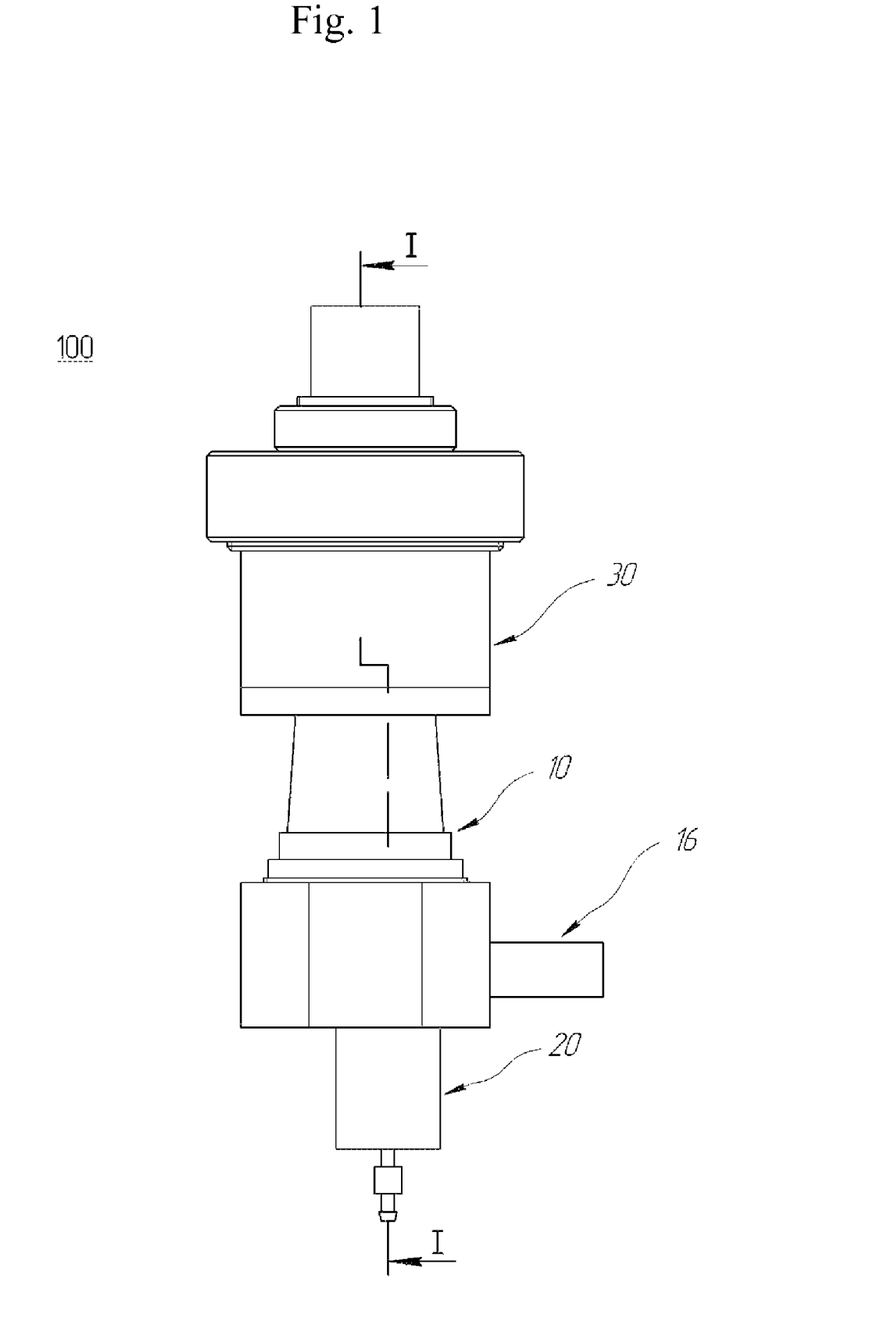
FIG. 1 is side perspective view of an exemplary embodiment of an apparatus for collecting airborne particles.
Figure 2:
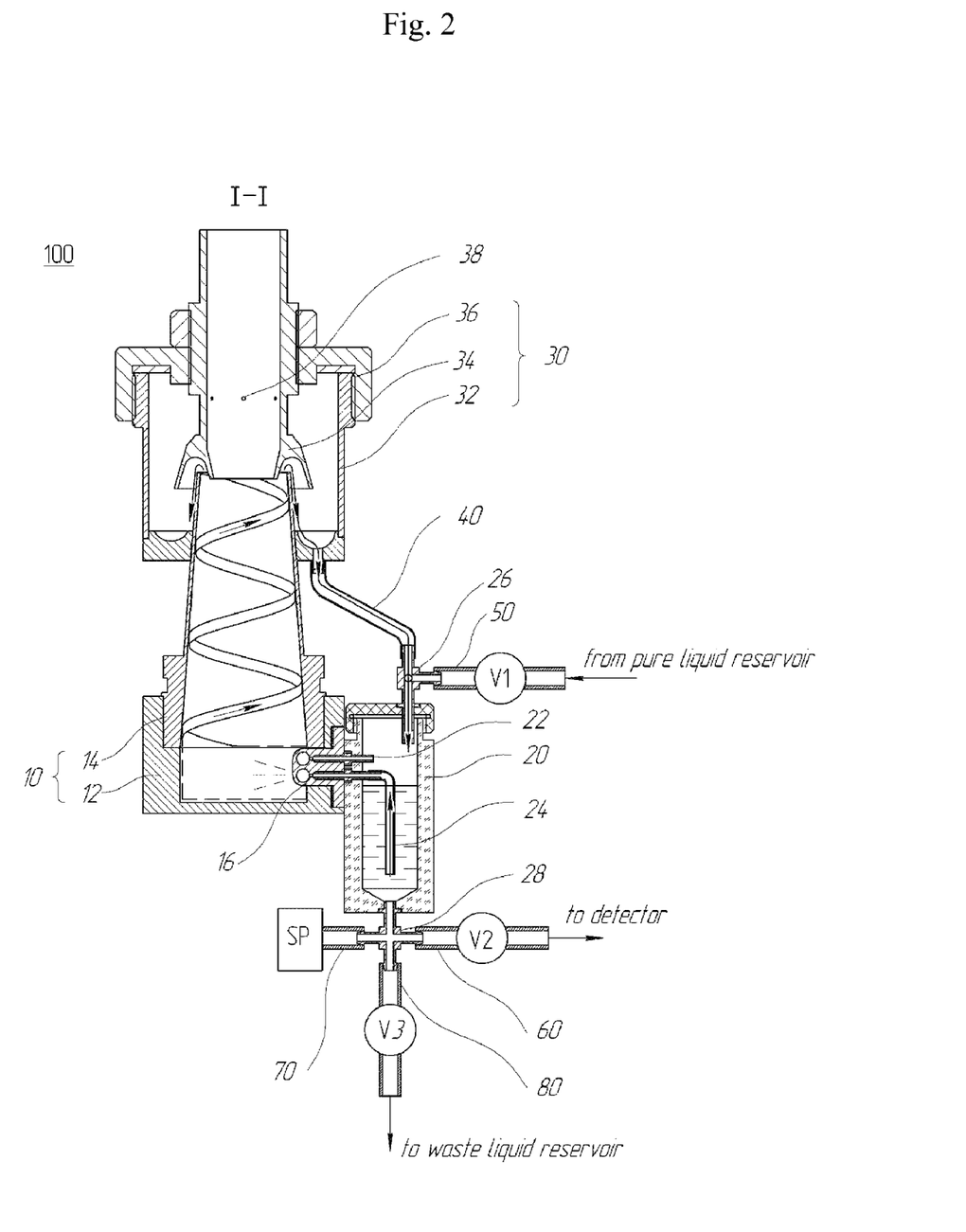
FIG. 2 is a partial cross-sectional view of taken along line I-I of FIG. 1.
Figure 3:
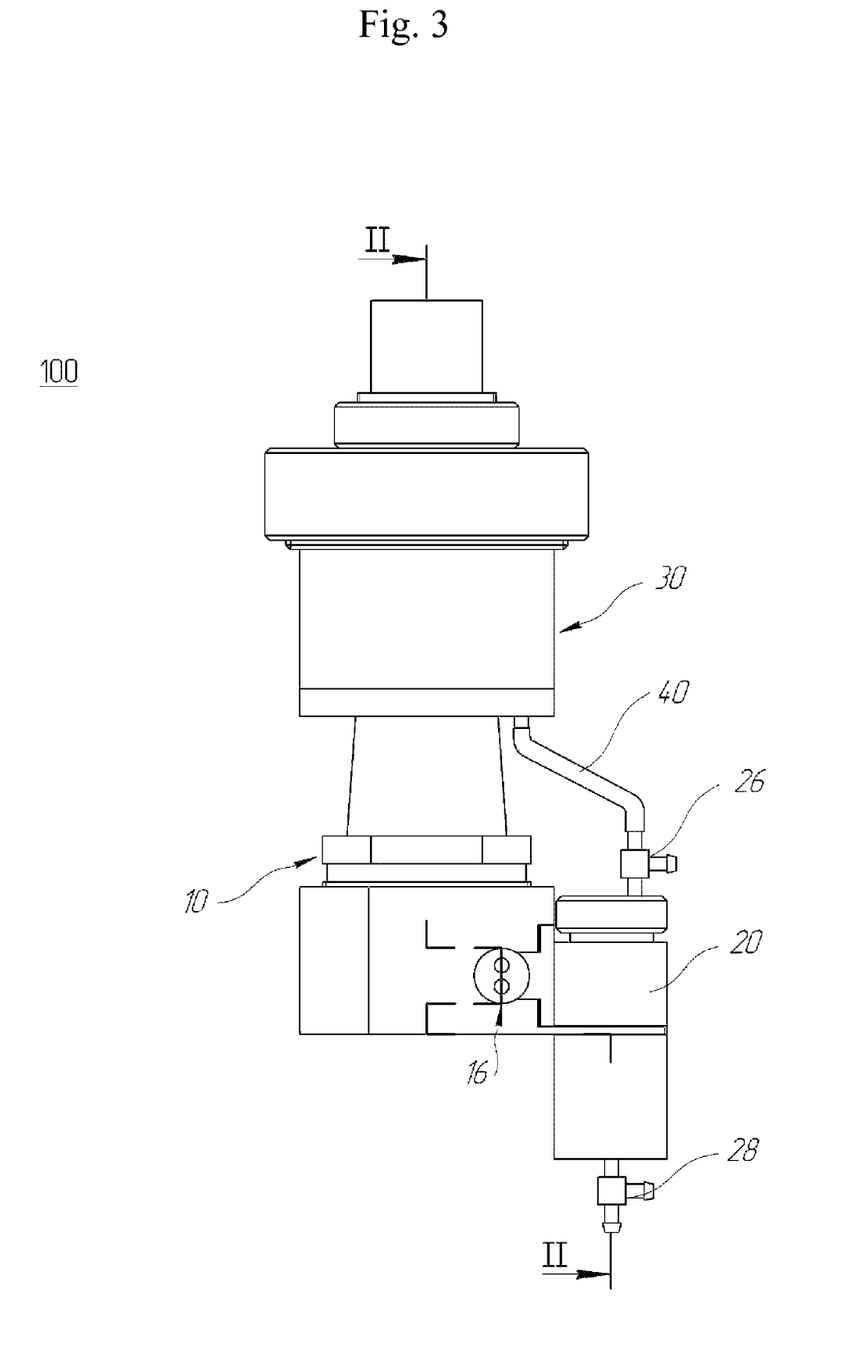
FIG. 3 is an alternative side perspective view of an exemplary embodiment of an apparatus for collecting airborne particles.
Figure 4:
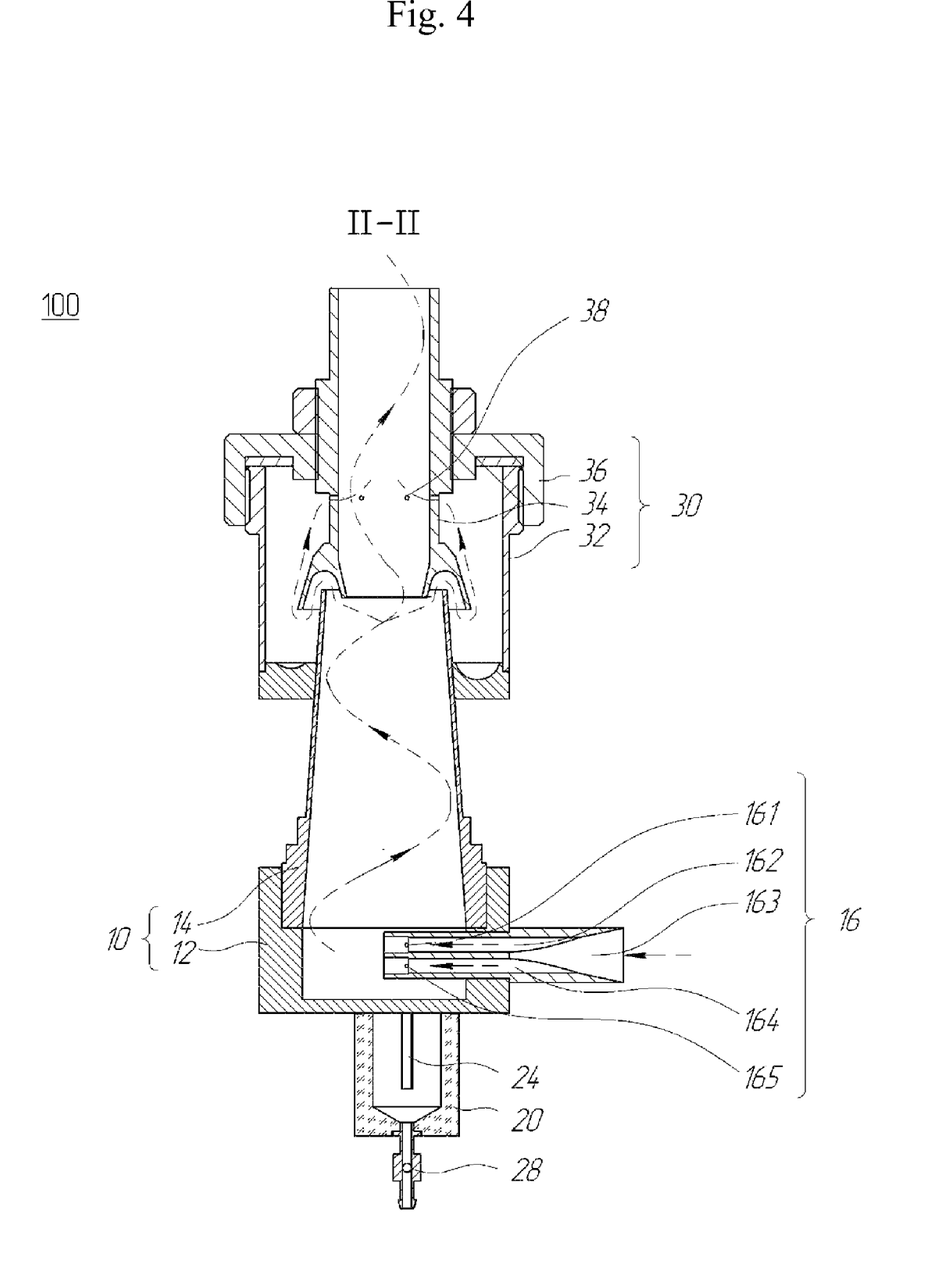
FIG. 4 is a partial cross-sectional view taken along line II-II of FIG. 2.

FIG. 1 is side perspective view of an exemplary embodiment of an apparatus for collecting airborne particles, FIG. 2 is a partial cross-sectional view taken along line I-I of FIG. 2, FIG. 3 is an alternative side perspective view of an exemplary embodiment of an apparatus for collecting airborne particles, and FIG. 4 is a partial cross-sectional view taken along line II-II of FIG. 3.

Referring to FIG. 1, a collecting apparatus 100 for airborne particles includes a cyclone 10 into which external air flows via an intake manifold 16; a reservoir 20, e.g., a cartridge 20, is disposed at an outer lower part of the cyclone 10 to supply an absorbing liquid to the cyclone 10, and a collector 30 is disposed at an upper part of the cyclone 10 to recirculate the absorbing liquid inside the collecting apparatus 100.

A feedback pipe 40 is connected to the cartridge 20 through an inlet supply fitting 26 and to the collector 30 to transport absorbing liquid from the collector 30 to the cartridge 20, as shown in FIG. 2.

Referring to FIGS. 2 and 4, the cyclone 10 according to an exemplary embodiment includes a swirling chamber 12 having a cylindrical space therein, and a precipitating chamber 14 disposed at an upper part of the swirling chamber 12 and having a conical internal space therein. In an internal volume of the cyclone 10, negative differential pressure is created by a vacuum pump (not shown) which forms a substantially spiral-shaped air whirlwind inside the cyclone 10 and a spiral tape of liquid film thereby forms on an inner wall of the cyclone 10. A pressure drop in the cyclone 10 is sufficient such that the spiral tape of liquid film reaches an upper section of the precipitating chamber 14 and thereafter flows over, e.g., out of the precipitating chamber 14, to enter the collector 30, as shown in FIGS. 2 and 4.

The intake manifold 16 is disposed in, e.g., protrudes into, the swirling chamber 12. As a result, an outlet section of the intake manifold 16 forms a tangential connection with a circle defined by a cross section of the swirling chamber 12. In addition, the outlet section includes two channels 162 and 164 (FIG. 4). As shown in FIG. 4, the two channels 162 and 164 are independent. Further, flat, vertically extending outlet nozzles of each of the two channels 162 and 164 include orifices. Referring still to FIG. 4, a common inlet conical nozzle 163 is disposed at an entrance of the intake manifold 16, whereby the two channels 162 and 164 are united. In an exemplary embodiment, external air from and external source (not shown) is supplied to, e.g., is aspirated inside, the collecting apparatus 100 through the common inlet conical nozzle 163. The two channels 162 and 164 according to an exemplary embodiment are substantially the same. Moreover, the two channels 162 and 164 may each be substantially cylindrical tubes with step change increases of respective channel diameters from an entrance thereof to an area inside the swirling chamber 12. An upper air ejector 161 and a bottom liquid ejector 165 are connected by means of ejector tubes 22 and 24, respectively, with an internal area of the cartridge 20 (FIG. 2) at a location corresponding to the step change of the nozzle orifice diameters (FIG. 4).

In an exemplary embodiment, the cartridge 20 is detachably installed at an outer side of the swirling chamber 12 of the cyclone 10, and is filled with an absorbing liquid for collecting airborne particles disposed in a collected sample of external air. More specifically, for example, the cartridge 20 may be snap-fitted onto the cyclone 10, but alternative exemplary embodiments are not limited thereto.

The cartridge 20 is also connected to other components of the apparatus 100 by means of the inlet supply fitting 26 and the outlet drainage fitting 28 (FIG. 2), as described above.

More specifically, a first nipple of the inlet supply fitting 26 is connected to the feedback tube 40, and a second nipple of the inlet supply fitting 26 is connected to a feed tube 50, to which a via electro-valve V1 is connected to thereby connect the cartridge 20 with an outer tank such as a pure liquid reservoir (not shown) for supplying fresh absorbing liquid to the cartridge 20. The outer tank allows for periodical refilling of absorbing liquid to the cartridge 20 to make up for losses due to evaporation and taking samples, for example.

The ejector tube 24, which transports absorbing liquid to the cyclone 10, extends across a sidewall of the cartridge 20, as shown in FIG. 2. In an exemplary embodiment, the ejector tube 24 is an aspiration ejector pipe 24, and absorbing liquid is aspirated through the aspiration ejector pipe 24 to flow into the bottom liquid ejector nozzle 165 of the intake manifold 16. As a result, the absorbing liquid is atomized due to a negative differential pressure which occurs at the step change area of the diameter of the channel 164 when input airflow is blown up, e.g., is applied. The aspiration ejector pipe 24 according to an exemplary embodiment is bent and extends downward into the reservoir volume, as shown in FIG. 2, such that absorbing liquid is carried even when a level of the absorbing liquid is decreased.

A sampling pipe 60 is attached to a first nipple of an outlet drainage fitting 28 to carry aliquots, e.g., portions, of the absorbing liquid to a detector (not shown). In an exemplary embodiment, the aliquots are very small portions of the absorbing liquid and the detector determines a concentration of airborne particles in the absorbing liquid based on an analysis of the aliquots. Further, an exemplary embodiment includes a valve V2 which is a micro valve and which regulates a volume of the aliquots of the absorbing liquid carried to the detector. The valve V2 may be installed in the sampling pipe 60, as shown in FIG. 2.

A drain pipe 80 is installed on a second nipple of the outlet drainage fitting 28 to allow discharge of contaminated absorbing liquid from the cartridge 20 into a waste tank such as a waste liquid reservoir (not shown). Valve V3 regulates a volume of the waste, e.g., contaminated, absorbing liquid discharged to the waste tank, and may be installed on the drain pipe 80, as shown in FIG. 2.

In an exemplary embodiment, a sensor SP for measuring a level of the absorbing liquid may be installed using a tube 70 and a third nipple of the drainage fitting 28 in the cartridge 20. Specifically, a pressure sensor SP may be used as the sensor SP, but alternative exemplary embodiments are not limited thereto.

Still referring to FIGS. 1-4, the collector 30 includes a collecting tank 32 disposed above the precipitating chamber 14 of the cyclone 10, a separator 34 disposed apart, at a predetermined interval, from the upper portion of the precipitating chamber 14 of the cyclone 10, and a cap 36 which seals the collecting tank 32. An upper part of the separator 32 includes a substantially cylindrical-shaped outlet manifold which passes through the cap 36 of the cyclone 10 to connect the collecting apparatus 100 with an outer vacuum pump (not shown).

Orifices 38 are provided along a periphery of the cylindrical outlet manifold under the cap 36 of the cyclone 10 to allow airflow to enter the collector 30 through the separator 34.

In an exemplary embodiment, the collecting tank 32 collects the absorbing liquid film flowing along the wall face of the precipitating chamber 14 and overflowing into the upper section thereof. A bottom face of the collecting tank 32 has a slant groove along a perimeter thereof for collecting the absorbing liquid at a point where the collecting tank 32 connects to the feedback pipe 40 (FIG. 2) to prevent collecting the absorbing liquid in the reservoir 32.

In an exemplary embodiment, the separator 34 prevents the absorbing liquid from spraying upward from the precipitating chamber 14. The separator 34 may be disposed such that it annularly surrounds inner and outer walls of the precipitating chamber 14 at the upper part thereof, as shown in FIGS. 2 and 4.

The feedback pipe 40 is connected to a bottom portion of the collecting tank 32 and to the inlet supply fitting 26 at an upper wall of the cartridge 20.

Hereinafter, an operation of an apparatus for collecting airborne particles in accordance with an exemplary embodiment will be described in further detail with reference to FIGS. 2 to 4.

A vacuum pump (not shown) is connected to an outlet manifold of the separator 34 and is switched on. The vacuum pump starts pumping air through the cyclone 10. An aerosol flow thereby goes through the intake manifold 16 and is divided into 2 streams by independent channels 162 and 164 and thereafter enters the swirling chamber 12.

The bottom liquid ejector 165 in the independent channel 164 of the intake manifold 16, disposed in the area of the step change of the internal channel diameter acts as an ejecting element, since the step change in the internal channel diameter assures a sufficient reduction of air pressure through the nozzle. As a result an aspiration of absorbing liquid occurs in the ejector tube 24 from the cartridge 20. An energy of airflow aspirated in the independent channel 164 causes atomization of the aspirated absorbing liquid jet in the bottom liquid ejector 165 thereby generating a liquid-drop aerosol flow. Therefore, in an area proximate to the outlet of the independent channel 164 section of the intake manifold 16, interaction intake air and the absorbing liquid takes place and liquid-drop aerosol flow is thereby observed, and as a result, aerosol particles from the intake airflow are deposited on surfaces of larger particles of the liquid-drop aerosol flow, thereby enhancing a capturing efficiency of the collecting apparatus 100 according to an exemplary embodiment, as the above-mentioned process is initiated directly in the independent channel 164 of the intake manifold 16.

Since the intake manifold 16 is tangentially introduced to the swirling chamber 12, aerohydro-dispersed swirling flow is generated in the chamber and, as a result, liquid is precipitated on the inner surface of the chamber and forms the continuous rotating film of absorbing liquid. Negative pressure in the collecting apparatus 100 created by the outer vacuum pump forces the liquid film to rise along the inner wall of precipitating chamber 14 in the form of a wide spiral band, as shown FIG. 2. Based on an intake airflow volume consumption, geometric sizes of the intake manifold 16, the swirling chamber 12 and the precipitating chamber 14 of the cyclone 10, the spiral band of liquid reaches the top of precipitating chamber 14, and smoothly flows over the edge onto collector 30. Thereafter, the spiral band of liquid flows through the feedback tube 40, enters the cartridge 20, and thereby provides a continuous re-circulation of the absorbing liquid in collecting apparatus 100 according to an exemplary embodiment.

Swirling airflow, under the effect of the negative differential pressures inside the cyclone 10, rises up in the form of a spiral flow as well, rotating around an axis of the cyclone. Due to a considerable difference in density and viscosity between air and liquid, respective speeds of rotation, and therefore revolutions per minute ("rpm") of two spiral flows, e.g., air flow and liquid flow, are considerably different from each other.

Thus, a process of precipitation of airborne particles from airflow is regulated by two mechanisms.

In the upper part of the swirling chamber 12, as well as in the bottom part of the precipitating chamber 14, precipitation is provided by impact of particles with the formed liquid film surface. In addition, a mechanism of precipitation defined by a tangential constituent of whirlwind rotation speed inside cyclone 10, exposed to centrifugal forces, aerosol particles are thrown toward and onto the walls of the cyclone 10, where they are captured by the rotating liquid film. The larger a tangential constituent of a rotation speed, the stronger centrifugal forces will be, and, as a result, the collection apparatus 100 according to an exemplary embodiment captures aerosol particles of substantially smaller diameter than a conventional apparatus. To maintain a constant value of centrifugal forces, the precipitating chamber 14 includes a substantially truncated cone shape along the axis of the whirlwind.

As described above, the absorbing liquid collected at the bottom of the collecting tank 32 flows in through a slant groove proximate to an area where the feedback pipe 40 enters the collector 30, and then goes on to the cartridge 20. If the absorbing liquid flows only under gravity forces, it accumulates on the bottom of collecting tank 32, thereby causing unpredictable losses of liquid and errors in evaluation of the sample.

To effectively eliminate and/or prevent this from occurring in an exemplary embodiment, the independent channel 162 of the intake manifold 16 is connected to the ejector tube 22 via the upper air ejector 161.

At the expense of intake airflow energy in air channel 162 of intake manifold 16 and a step in a diameter of the independent channel 162, a negative pressure differential occurs in the ejector tube 22 and in an upper air volume of the cartridge 20 at a point of connection of the inlet supply manifold 26 thereto and, therefore, in the feedback tube 40 as well, thereby causing forced aspiration of recirculating collection liquid from the collecting tank 32 to the cartridge 20, thereby effectively preventing its accumulation in the collecting tank 32.

A design of the outlet section of the intake manifold 16 is such that, at the expense of using two vertically-positioned channels 162 and 164, e.g., one under the other, each has a flat form substantially rectangular in shape, thereby providing a substantially improved capture of aerosol, based on cyclone theory. Therefore, exemplary embodiments provide a narrow and flat structure rotating airflow inside the cyclone 10. Thus, the flow, according to cyclone theory, provides a substantially improved capture of aerosol particles from the air stream.

In addition, in the collection apparatus 100 according to an exemplary embodiment, the separator 34 separates air and liquid flows, which divides the respective flows near the upper section of the precipitating chamber 14 of the cyclone 10, thus effectively preventing blowout of recirculating collecting liquid drops, albeit at the expense of energy of upstream air. A spacing size of belts of the separator 34 in the upper section of the precipitating chamber 14 are adjusted to provide a smooth flow of re-circulating liquid over the upper section of the precipitating chamber 14 while also effectively preventing drop formation therein.

In an exemplary embodiment, a small portion of output airflow passing through the separator 34 flows back through the orifices 38 in the wall of outlet manifold of the separator 32.

To take samples of absorbing liquid for analysis of a composition and concentration of sampled aerosol, valve V2, installed in sampling tube 60, is opened for a predetermined time. To provide continuous operation of the collecting apparatus 100, re-filling absorbing liquid in cartridge 20 via electro-valve V1 installed in the supply tube 50 is opened, and a required volume of fresh absorbing liquid is supplied to the cartridge 20 from the outer tank (not shown). Upon completion of the operation of the collecting apparatus 100, contaminated absorbing liquid flows through the drying tube 80 from cartridge 20 after valve V3 is switched on.

Control of a level of absorbing liquid in the cartridge 20 is performed based on the sensor SP connected through the tube 70 and the drainage fitting 28 to the bottom of the cartridge 20. The sensor SP converts a measurement of a liquid column height in the cartridge 20 into an electric signal proportional thereto. Thus, assessment of a contamination level liquid in the cartridge 20 is performed directly in the detector during analysis of supplied aliquots of absorbing liquid.

Figure 5:
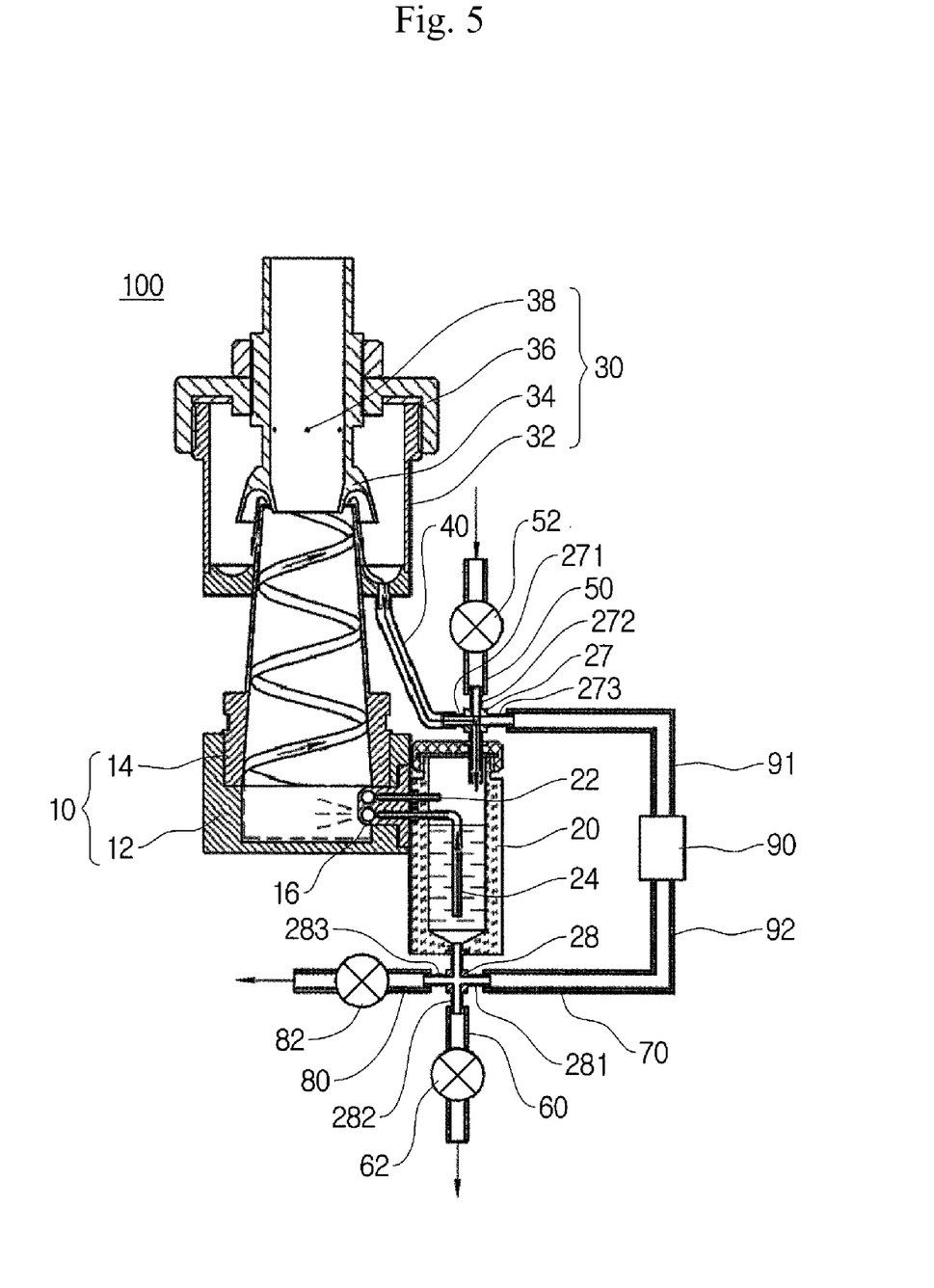
FIG. 5 is a partial cross-sectional view of an alternative exemplary embodiment of an apparatus for collecting airborne particles.

FIG. 5 is a partial cross-sectional view of an alternative exemplary embodiment of an apparatus for collecting airborne particles. The same reference characters in FIG. 5 denote the same or like components as described above in greater detail with reference to FIGS. 1-4, and any repetitive detailed description thereof has hereinafter been omitted.

Referring to FIG. 5, an apparatus for collecting airborne particles 100 according to an alternative exemplary embodiment includes a 3-way supply fitting 27 in the upper part of the cartridge 20. A first inlet nipple 271 of the 3-way supply fitting 27 is connected to the feedback pipe 40, a second inlet nipple 272 of the 3-way supply fitting 27 is connected to the supply pipe 50, and a third inlet nipple 273 of the 3-way supply fitting 27 is connected to a first control pipe 91 which is connected to an upper part of a level sensor 90.

Further, a first outlet nipple 281 of a 3-way drain fitting 28 installed on a lower part of the cartridge 20 is connected to a second control pipe 92 connected to a lower part of the level sensor 90, a second outlet nipple 282 is connected to the sampling pipe 60, and a third outlet nipple 283 is connected to the drain pipe 80.

Figure 6:
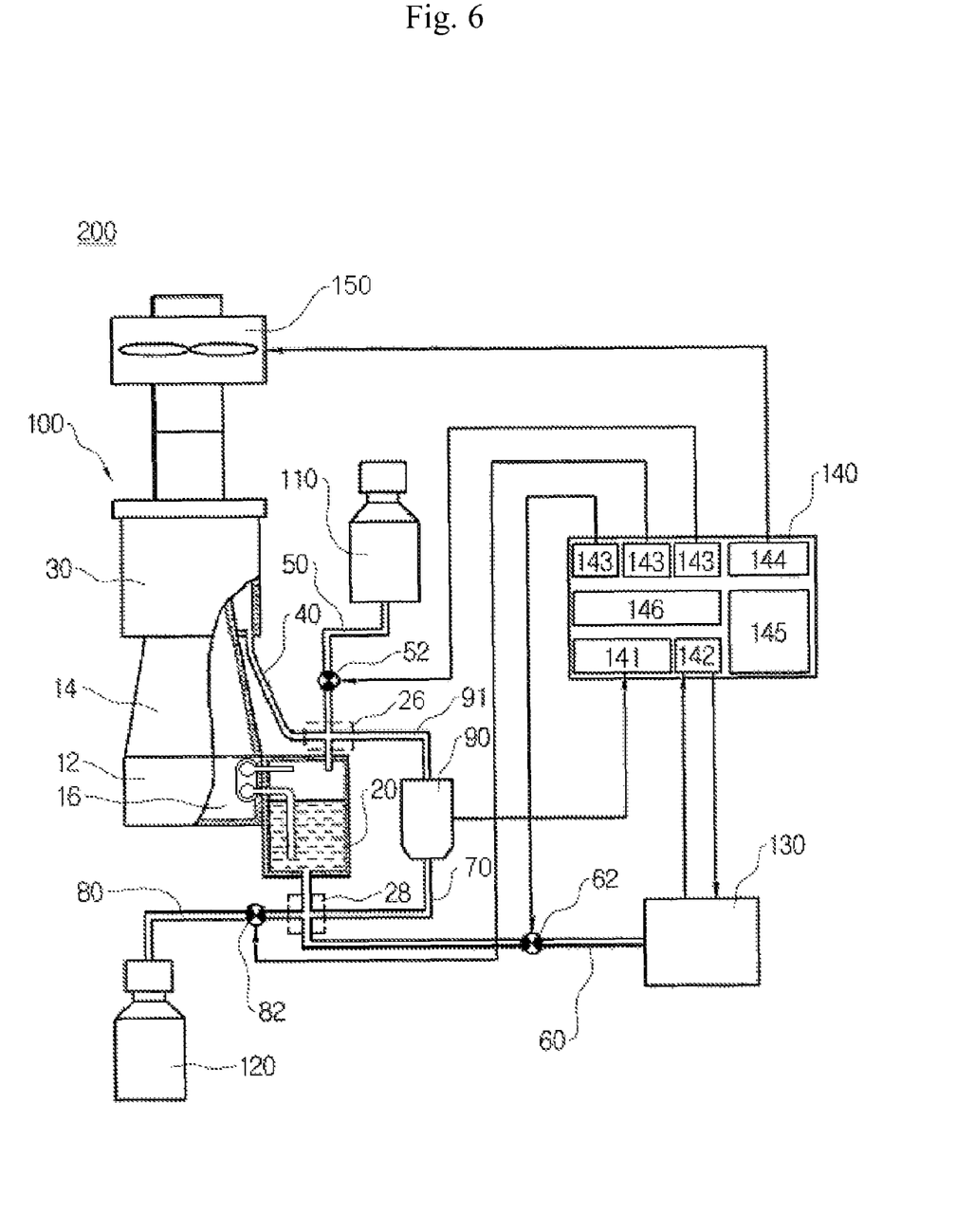
FIG. 6 is a plan view of an exemplary embodiment of a system for collecting and detecting airborne particles.

FIG. 6 is a plan view of an exemplary embodiment of a system for collecting and detecting airborne particles.

Referring to FIG. 6, a system for collecting and detecting airborne particles 200 according to an exemplary embodiment includes the apparatus for collecting airborne particles 100, a supplementary reservoir 110, a drain reservoir 120, a microbiological detector 130, a level sensor 90 and a microcontroller 140.

In addition, a peristaltic filling pump 52, a peristaltic sampling pump 62 and a peristaltic draining pump 82 are installed on the feed tube 50, the sampling pipe 60 and the drain pipe 80, respectively.

When a level of the absorbing liquid in the cartridge 20 falls, the supplementary reservoir 110 increases the level (to maintain an overall level at a predetermined level) by supplying clean absorbing liquid to the cartridge 20. Specifically, the supplementary reservoir 110 is connected to the cartridge 20 through the feed tube 50. The peristaltic filling pump 52 installed on the feed tube 50 transports the absorbing liquid in the supplementary reservoir 110 to the cartridge 20.

The drain reservoir 120 is connected to the cartridge 20 through the drain pipe 80, and receives contaminated absorbing liquid from the cartridge 20 when a contamination of the absorbing liquid reaches a predetermined level. The peristaltic draining pump 82 is installed on the drain pipe 80 to transport the contaminated absorbing liquid from the cartridge 20 to the drain reservoir 120.

The microbiological detector 130 analyzes a sample of the contaminated absorbing liquid inside the cartridge 20 to measure a level of microbe contamination in the absorbing liquid. The microbiological detector 130 is connected to the cartridge 20 by the sampling pipe 60, and the peristaltic sampling pump 62 installed on the sampling pipe 60 transports an aliquot of the contaminated absorbing liquid from the cartridge 20 to the microbiological detector 130.

In addition, the level sensor 90 detects a level of the absorbing liquid inside the cartridge 20. A first end of the level sensor 90 is connected to the upper part of the cartridge 20 through the first control pipe 91, and a second end is connected to the lower part of the cartridge 20 through the second control pipe 92. In an exemplary embodiment, a membrane pressure sensor SP (FIGS. 1-4) is used as the level sensor 90.

The microcontroller 140 controls operation of the peristaltic filling pump 52, the peristaltic sampling pump 62, the peristaltic draining pump 82 and a vacuum pump 150 which pumps air through the collecting apparatus 100 in response to electrical signals from the level sensor 90 and the detector 130. In an exemplary embodiment, the microcontroller 140 includes an analog-to-digital ("A/D") converter 141, a processor 142, switches 143, a relay 144, a keyboard 145 for manual inputs and a display 146.

The A/D converter 141 is connected to the level sensor 90 and transforms electrical signals from the level sensor 90 into a digital signal. The processor 142 orders corresponding collecting apparatus 100 assembly operation changes based on measurements of contamination level by the microbiological detector 130. The switches 143 are connected to the peristaltic filling pump 52, peristaltic draining pump 82 and the peristaltic sampling pump 62 and turn on and/or off the peristaltic filling pump 52, drain pump 82 and the peristaltic sampling pump 62 based on signals from the processor 142. The relay 144 is connected to the vacuum pump 150 and turns on and/or off the vacuum pump 150, also based on signals from the processor 142.

Figure 7:
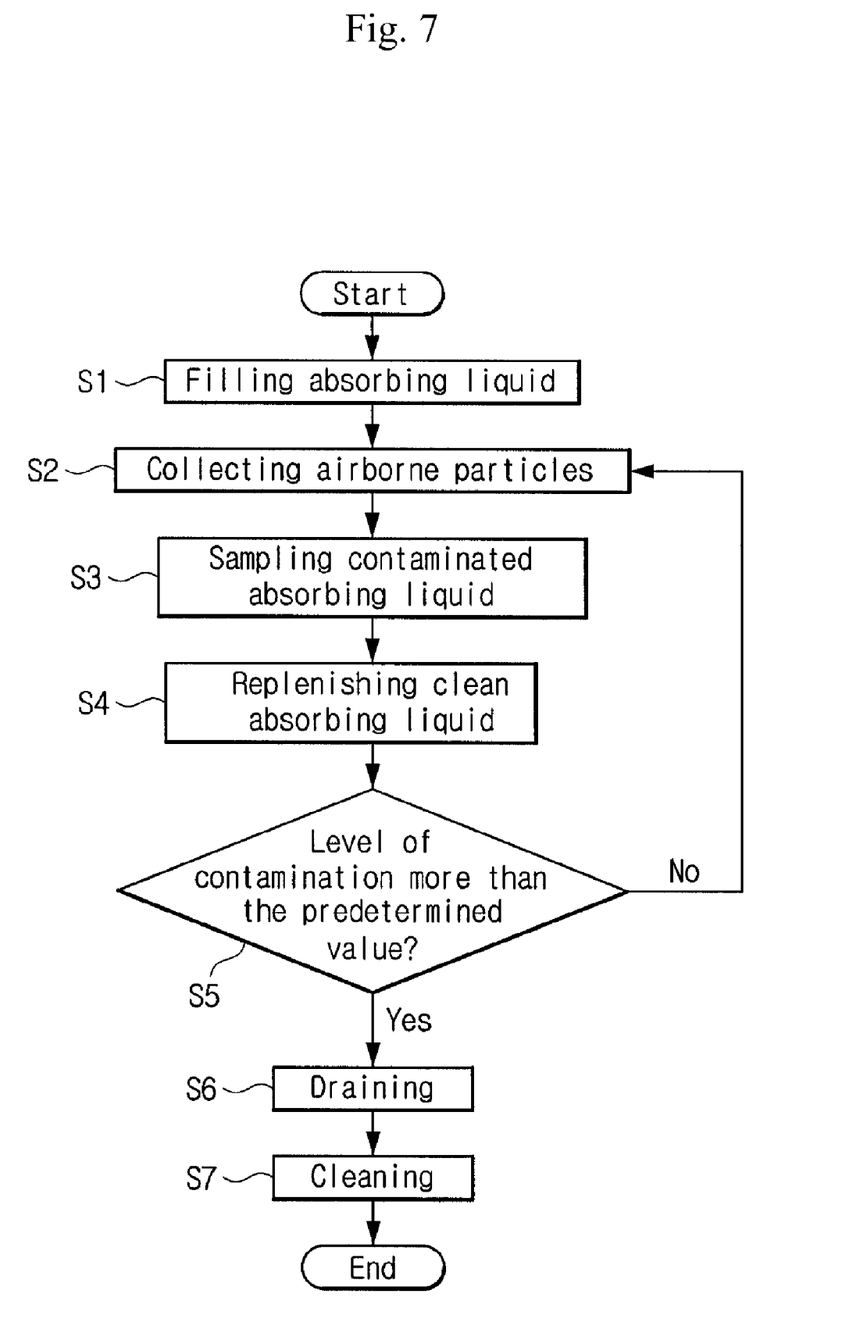
FIG. 7 is a flowchart illustrating an operation of the exemplary embodiment of the system for collecting and detecting airborne particles shown in FIG. 6.

FIG. 7 is a flowchart illustrating an operation of the exemplary embodiment of the system for collecting and detecting airborne particles shown in FIG. 6.

Referring to FIGS. 6 and 7, in step S1, when a "start" button on the keyboard 145 is pressed, the microcontroller 140 operates the peristaltic filling pump 52 to fill the cartridge 20, initially empty, with clean absorbing liquid. When a predetermined liquid level inside the cartridge 20 is achieved, the peristaltic filling pump 52 stops its operation.

In an exemplary embodiment, there is a brief waiting period for stabilizing the system after the peristaltic filling pump 52 stops operating.

In step S2, the microcontroller 140 operates the vacuum pump 150 and operates the collecting device 100. Airborne particles in the air are captured by the absorbing liquid as the collecting device 100 operates, as described above in greater detail. The collecting device 100 stops after a determined time, e.g., one cycle of air sampling. In an exemplary embodiment, one cycle may be approximately 10 minutes, but alternative exemplary embodiments are not limited thereto.

After the collecting device 100 stops operating, there is a brief waiting period for stabilizing the system. Then, in step S3, the microcontroller 140 operates the peristaltic sampling pump 62 to extract an aliquot of the contaminated absorbing liquid inside the cartridge 20 and sends the aliquot to the microbiological detector 130.

Meanwhile, the level sensor 90 detects a current level of absorbing liquid in the cartridge 20 and sends the detected current level to the processor 142. If the measurement is less than a predetermined value, the processor 142 operates the peristaltic filling pump 52, through the switch 143, to supply clean absorbing liquid from the supplementary reservoir 110 to the cartridge 20 (step S4).

In step S5, the microbiological detector 130 measures a level of contamination of the sample of absorbing liquid and sends the measurement to the processor 142. The processor 142 determines whether the measurement of the level of contamination of the sampled absorbing liquid is equal to or greater than a predetermined limit value.

If the level of contamination of the absorbing liquid is equal to or greater than the predetermined limit value, the processor 142 operates the peristaltic draining pump 82 using the switch 143 and transports all of the absorbing liquid inside the cartridge 20 to the drain reservoir 120 (step S6). If the level of contamination of the absorbing liquid is less than the predetermined limit value, the processor 142 repeats the above described cycle of air sampling with the collecting device 100 until the level of contamination of the sampled absorbing liquid reaches the predetermined limit value or higher.

When all of the absorbing liquid inside the cartridge 20 is drained, the microcontroller 140 operates the peristaltic filling pump 52 and transports a predetermined amount of pure absorbing liquid from the supplemental reservoir 110 to the cartridge 20. A portion of an amount of pure absorbing liquid supplied is for flushing the collecting device 100. When the cartridge 20 is filled with absorbing liquid, the microcontroller 140 operates the vacuum pump 150. Thus, outside air does not enter into the cyclone 10 of the collecting device 100 and only the pure absorbing liquid enters into the cyclone 10 (step S7).

After cleaning the device 100 for a predetermined amount of time, the microcontroller 140 turns off the vacuum pump 150 and turns on the peristaltic draining pump 82 to drain the absorbing liquid for cleaning, thereby completing operation of the system for collecting and detecting concentration of airborne particles 200 according to an exemplary embodiment.

Thus, according to exemplary embodiments as described herein, a system for collecting and detecting airborne particles allows a user to automatically collect and detect the airborne parties in a substantially improved, easy-to-use manner.

The present invention should not be construed as being limited to the exemplary embodiments set forth herein. Rather, these exemplary embodiments are provided so that this disclosure will be thorough and complete and will fully convey the concept of the present invention to those skilled in the art.

Although the present invention has been particularly shown and described herein with reference to exemplary embodiments thereof, such exemplary embodiments are for illustrative purposes, and it will be understood by those of ordinary skill in the art that various changes in form and details made be made therein without departing from the scope or spirit of the present invention as defined by the following claims.

What is claimed is:

1. An apparatus for collecting airborne particles comprising:
    a cyclone into which external air and an absorbing liquid are introduced for collecting the airborne particles in the external air with the absorbing liquid;
    a reservoir in fluid communication with the cyclone and which stores the absorbing liquid to be sprayed into the cyclone as an absorbing liquid film;
    a collector in fluid communication with the cyclone and which collects the absorbing liquid film from the cyclone;
    a feedback pipe in fluid communication with the collector and the reservoir and which transports the absorbing liquid film collected in the collector to the reservoir; and
    an intake manifold tangentially introduced in the cyclone.

2. The apparatus according to claim 1, wherein
    the cyclone comprises a swirling chamber and precipitating chamber, and
    the collector collects the absorbing liquid film flowing along an inner wall of the precipitating chamber.

3. The apparatus according to claim 2, wherein the swirling chamber has a cylinder shape.

4. The apparatus according to claim 2, wherein
    the precipitating chamber has a shape of a truncated cone, and
    a lower portion of the precipitating chamber is coaxially connected to an upper portion of the swirling chamber.

5. The apparatus according to claim 2, further comprising an intake manifold in fluid communication with the cyclone, wherein the intake manifold comprises:
    a first cylindrical channel and a second cylindrical channel disposed vertically adjacent to the first cylindrical channel; and
    a conical inlet nozzle common to both the first cylindrical channel and the second vertical channel.

6. The apparatus according to claim 5, wherein the intake manifold is connected to the swirling chamber tangential to an inner diameter of the swirling chamber.

7. The apparatus according to claim 5, wherein each of the first cylindrical channel and the second cylindrical channel includes a step increase in a diameter thereof proximate to an outlet section thereof.

8. The apparatus according to claim 7, wherein
    the first cylindrical channel is disposed above the second cylindrical channel;
    the first cylindrical channel comprises an air ejector nozzle disposed proximate to the step increase in the diameter of the first cylindrical channel, and
    the second cylindrical channel comprises a liquid ejector nozzle disposed proximate to the step increase in the diameter of the second cylindrical channel.

9. The apparatus according to claim 1, wherein the reservoir is detachably connected to the cyclone.

10. The apparatus according to claim 2, wherein the collector comprises:
    a separator disposed apart from an upper portion of the precipitating chamber of the cyclone to separate flow of the absorbing liquid film from air flow in the cyclone; and
    a collecting tank which collects the absorbing liquid film separated by the separator.

11. The apparatus according to claim 10, wherein the separator has an annular shape which surrounds inner and outer walls of the precipitating chamber of the cyclone along a periphery of the upper portion of the precipitating chamber.

12. The apparatus according to claim 10, wherein
    the collecting tank comprises a spiral-shaped slant groove disposed in a lower surface thereof, and
    the feedback pipe is connected to the collecting tank using the spiral-shaped slant groove.

13. The apparatus according to claim 9, further comprising a supply fitting connected to the reservoir, wherein the supply fitting comprises a first inlet nipple, a second inlet nipple and a third inlet nipple.

14. The apparatus according to claim 13, wherein the first inlet nipple of the supply fitting is connected to the collector by the feedback pipe.

15. The apparatus according to claim 14, wherein the second inlet nipple of supply fitting is connected to a supply pipe to supply clean absorbing liquid to the reservoir.

16. The apparatus according to claim 15, further comprising a valve disposed in the supply pipe and which regulates an inflow of the clean absorbing liquid from an outer tank to the reservoir.

17. The apparatus according to claim 9, further comprising a drainage fitting connected to the reservoir, wherein the drainage fitting comprises a first outlet nipple, a second outlet nipple and a third outlet nipple.

18. The apparatus according to claim 17, wherein a sensor for measuring a level of the absorbing liquid in the reservoir is connected to the first outlet nipple of the drainage fitting.

19. The apparatus according to claim 17, further comprising:
    a detector in fluid communication with the reservoir; and
    a sampling pipe connected to the second outlet nipple of the drainage fitting, wherein the sampling pipe transports an aliquot of the absorbing liquid to the detector to detect a concentration of the airborne particles collected by the absorbing liquid film.

20. The apparatus according to claim 19, further comprising a valve disposed in the sampling pipe, wherein the valve regulates a flow of the absorbing liquid from the reservoir to the detector.

21. The apparatus according to claim 17, further comprising a drain pipe connected to the third outlet nipple of drainage fitting.

22. The apparatus according to claim 21, further comprising a valve disposed in the drain pipe, wherein the valve regulates a flow of the absorbing liquid from the reservoir to a waste tank.

23. The apparatus according to claim 1, wherein the airborne particles comprise microbes.

24. A method of collecting airborne particles, the method comprising:
supplying external air and an absorbing liquid to an internal space of a cyclone tangentially;
mixing the external air and the absorbing liquid to form an absorbing liquid film on an inner wall of the cyclone;
collecting airborne particles in the external air with the absorbing liquid film formed;
collecting the absorbing liquid film in which the airborne particles are collected; and
dispersing and remixing the absorbing liquid film with input airflow inside an intake manifold in fluid communication with the cyclone.

25. The method according to claim 24, wherein the supplying the external air and the dispersing and remixing the absorbing liquid film are based on a pressure difference inside the cyclone.

26. The method according to claim 24, further comprising collecting an aliquot of the absorbing liquid to determine a concentration of the airborne particles collected by the absorbing liquid film.

27. The method according to claim 24, further comprising measuring one of a level and a degree of pollution of the absorbing liquid.

28. A system for collecting airborne particles and detecting a concentration of the airborne particles by collecting the airborne particles with an absorbing liquid, the system comprising:
a cyclone, into which external air from an air source and an absorbing liquid are introduced for collecting the airborne particles with the absorbing liquid, wherein the cyclone the external air and the absorbing liquid undergo vortex mixing and atomization to precipitate airborne particles from the external air onto a surface of liquid film formed inside the cyclone;
a reservoir in fluid communication with the cyclone and which stores the absorbing liquid to be sprayed into the cyclone as an absorbing liquid film;
a collector disposed at an upper part of the cyclone in fluid communication with the cyclone, which collects the absorbing liquid film moving along an inner wall of the cyclone and which transports the absorbing liquid film back to the reservoir;
a supplementary reservoir connected to the reservoir and which supplies the absorbing liquid to the reservoir;
a drain reservoir connected to the reservoir and which receives the absorbing liquid from the reservoir; and
a detector connected to the reservoir and which measures a level of contamination of the absorbing liquid by sampling the absorbing liquid inside the reservoir.

29. The system according to claim 28, further comprising a level sensor connected to the reservoir and which detects a level of the absorbing liquid inside the reservoir.

30. The system according to claim 29, wherein the level sensor comprises a membrane pressure sensor.

31. The system according to claim 29, further comprising a three-way supply fitting disposed at an upper portion of the reservoir, wherein the three-way supply fitting comprises:
a first inlet nipple connected to a feedback pipe connected between the collector and the reservoir;
a second inlet nipple connected to a supply pipe connected to the supplementary reservoir; and
a third inlet nipple connected to a first control pipe connected to the level sensor.

32. The system according to claim 29, further comprising a three-way drain fitting disposed at a lower portion of the reservoir, wherein the three-way drain fitting comprises:
a first outlet nipple connected to a second control pipe connected to the level sensor;
a second outlet nipple connected to a sampling pipe connected to the detector; and
a third outlet nipple connected to a drain pipe connected to the drain reservoir.

33. The system according to claim 29, further comprising a microcontroller which controls an operation of a peristaltic filling pump, a peristaltic drain pump and a peristaltic sampling pump based on electrical signals from at least one of the detector and the level sensor.

34. The system according to claim 33, wherein the microcontroller comprises:
an analog-to-digital (A/D) converter connected to the level sensor;
a processor connected to the detector;
switches connected to the peristaltic filling pump, the peristaltic drain pump and the peristaltic sampling pump;
a relay connected to the air source;
an input unit; and
a display.

35. A method of collecting airborne particles and detecting a concentration of the airborne particles, the method comprising:
supplying absorbing liquid to a reservoir;
collecting the airborne particles in air with an absorbing liquid film supplied to a cyclone;
returning the absorbing liquid to a reservoir;
sampling the absorbing liquid inside the reservoir to measure a level of contamination thereof;
removing the absorbing liquid from the reservoir when the level of contamination thereof exceeds a predetermined value; and
supplying new absorbing liquid to the reservoir.

36. A method according to claim 35, wherein the collecting airborne particles comprises:
mixing the absorbing liquid and air in an intake manifold;
supplying the absorbing liquid and the air to a space inside the cyclone to form an absorbing liquid film therein;
absorbing the airborne particles with the absorbing liquid film;
collecting the absorbing liquid film containing the airborne particles in a collector; and
resending the absorbing liquid film in the collector to the intake manifold to remix the absorbing liquid with the air.

37. A method according to claim 35, further comprising:
measuring a level of the absorbing liquid in the reservoir; and
supplying additional absorbing liquid to the reservoir when a level thereof decreases.

* * * * *